United States Patent [19] [11] Patent Number: 4,861,932
Chen et al. [45] Date of Patent: Aug. 29, 1989

[54] AROMATIZATION PROCESS

[75] Inventors: Nai Y. Chen, Titusville, N.J.; Thomas F. Degnan, Yardley; Sharon B. McCullen, Newtown, both of Pa.

[73] Assignee: Mobil Oil Corp., New York, N.Y.

[21] Appl. No.: 140,274

[22] Filed: Dec. 31, 1987

[51] Int. Cl.$^4$ .................... C07C 12/00; C10G 35/06
[52] U.S. Cl. .................................. 585/412; 208/65; 585/417; 585/419
[58] Field of Search .................. 208/65; 585/412, 417, 585/419

[56] References Cited

U.S. PATENT DOCUMENTS

| | | | |
|---|---|---|---|
| 3,684,692 | 8/1972 | Keith et al. | 208/65 |
| 3,760,024 | 9/1973 | Cattanach . | |
| 3,843,741 | 10/1974 | Yan . | |
| 4,174,270 | 11/1979 | Mayes | 208/65 |
| 4,190,519 | 2/1980 | Miller et al. | 208/65 |
| 4,295,958 | 10/1981 | Mauldin et al. | 208/138 |
| 4,348,271 | 9/1982 | Swan | 208/138 |
| 4,350,835 | 9/1982 | Chester et al. . | |
| 4,579,831 | 4/1986 | Field | 502/66 |
| 4,590,322 | 5/1986 | Chu | 585/415 |

OTHER PUBLICATIONS

Pines, *The Chemistry of Catalytic Hydrocarbon Conversions*, Academic Press, New York (1981), pp. 102–111.
Rabo et al, "Sulfur-Resistant Isomerization Isomerization Catalyst: Study of Atomic Platinum Dispersions on a Zeolite Suport", Third International Congrss Catalysis, North Holland, Amsterdam, 1965 2:1329.
Gallezot et al, "Unusual Catalytic Behavior of Very Small Platinum Particles".
"Particles Engaged in Y Zeolites", Proceedings of the Sixth International Congress on Catalysis, Chemical Society, London, 2:696 (1977).
Tri et al, "Sulfur Resistance of Modified Platinum Y Zeolite", Studies in Surface Science and Catalysis, 5:279 (1980).

*Primary Examiner*—Curtis R. Davis
*Attorney, Agent, or Firm*—Alexander J. McKillop; Charles J. Speciale; Dennis P. Santini

[57] ABSTRACT

A process for converting a $C_2$–$C_{12}$ paraffinic hydrocarbon feed to aromatics comprising passing the feed through a first conversion zone wherein the feed contacts a noble metal/low acidity medium pore size zeolite catalyst, and then passing the resulting hydrocarbon mixture through a second conversion zone wherein the resulting hydrocarbon mixture contacts a medium pore size acidic zeolite catalyst.

26 Claims, No Drawings

AROMATIZATION PROCESS

FIELD OF THE INVENTION

The present invention relates to the production of aromatics. More particularly, the present invention relates to a process for converting nonaromatic $C_2$–$C_{12}$ paraffinic hydrocarbons to aromatics. Even more particularly, the present invention relates to a process for the manufacture of gasoline boiling range hydrocarbons by an improved aromatization process.

BACKGROUND OF THE INVENTION

Methods for producing gasoline boiling range aromatic hydrocarbons from nonaromatic hydrocarbon feeds by employing medium pore size zeolite type catalysts are generally known, as exemplified in, e.g., U.S. Pat. Nos. 3,760,024, 3,843,741 and 4,350,835. In such processes, the desired end product comprises primarily gasoline boiling range materials. The basic reaction is an aromatization reaction. Gasoline, as such term is used herein, and as such term is commonly used in the petroleum industry, is useful as a motor fuel for internal combustion engines. More specifically, gasoline is hydrocarbon in nature, and contains various aliphatic and aromatic hydrocarbons having a full boiling range of about 280° to 430° F., depending on the exact blend used and the time of year. Although gasoline is predominantly hydrocarbon in nature, various additives which are not necessarily exclusively hydrocarbon are often included. Additives of this type are usually present in very small proportions, e.g., less than 1% by volume of the total gasoline. Further, it is also not uncommon for various gasolines to be formulated with non-hydrocarbon components, particularly alcohols and/or ethers as significant, although not major, constituents thereof. Such alcohols, ethers and the like have burning qualities in internal combustion engines which are similar to those of hydrocarbons in the gasoline boiling range. For purposes of this specification and the present invention, however, the term "gasoline" denotes a mixture of hydrocarbons boiling in the aforementioned gasoline boiling range and is not intended to include the above-referred to additives and/or non-hydrocarbon constituents.

High octane gasoline is desirable for use with internal combustion engines from a standpoint of fuel efficiency, and thus is also attractive from an economic perspective. Further, the gradual phasing out of lead in gasoline has created a demand for new methods for obtaining high octane gasoline. It is known that aromatic gasoline boiling range hydrocarbons have high octane (R+O), (M+O) and/or (R+M)/2 values. It is known that gasoline octane is related to the aromatic selectivity of the catalyst employed in the reforming process used to produce gasoline boiling range hydrocarbons. An increase in aromatic selectivity will result in increased gasoline octane. Aromatic selectivity, as used throughout is defined as (wt. % aromatics produced)/(100-wt. % $C_2=+$) where $C_2=+$ is ethylene and high paraffins and olefins in the product.

Processes for converting paraffinic hydrocarbons to aromatics using a single conversion zone or reactor containing a noble metal/low acidity medium pore size zeolite catalyst are generally known, as are processes using a single conversion zone or reactor containing a medium pore size acidic zeolite catalyst, which may contain a dehydrogenation metal. Also, aromatization processes using two conversion zones containing the same or different catalysts in the same reactor or separate reactors are also known.

For economic reasons, there is a clear need to increase aromatic selectivity of catalysts employed in processes used to produce aromatics. Hence, methods which are capable of increasing aromatic selectivity of the catalyst are very desirable.

SUMMARY OF THE INVENTION

Accordingly, one object of the present invention is to provide an improved process for the production of aromatics.

Another object of the present invention is to provide an improved process for converting $C_2$–$C_{12}$ paraffinic hydrocarbons to aromatics.

Still another object of the present invention is to provide an improved aromatization process which produces gasoline boiling range hydrocarbons with increased aromatic selectivity.

A further object of the present invention is to provide an improved aromatization process capable of effectively suppressing hydrogenolysis and increasing aromatic selectivity.

Yet a further object of the present invention is to provide an improved aromatization process from an economical standpoint by increasing the gasoline octane of the aromatics produced thereby.

To achieve the foregoing objects and in accordance with its purpose, the present invention provides a process for converting a $C_2$–$C_{12}$ paraffinic hydrocarbon feed to aromatics by passing the feed through a first conversion zone wherein the feed contacts a noble metal/low acidity medium pore size zeolite catalyst, and then passing the resulting hydrocarbon mixture through a second conversion zone wherein the resulting hydrocarbon mixture contacts a medium pore size acidic zeolite catalyst.

Preferably, the noble metal/low acidity medium pore size zeolite catalyst employed in the first conversion zone contains a platinum group metal as the noble metal component selected from the group conssting of platinum, palladium, iridium, osmium, rhodium and ruthenium in an amount of from about 0.01 to about 10 wt. % based on the total weight of the metal and zeolite, and this low acidity zeolite has an alpha value of less than 5. Even more preferably, the platinum group metal comprises from 0.1 to 3.0 wt. %, and the low acidity zeolite has an alpha value of less than 1.

Preferably, the medium pore size acidic zeolite catalyst employed in the second conversion zone contains a dehydrogenation metal selected from the group consisting of Zn, Ga, Sn or Cr in an amount of from about 0.01 to about 10 wt. % based on the total weight of the metal and zeolite, and the acidic zeolite has an alpha value of greater than about 10. More preferably, the acidic zeolite has an alpha value between 50 and 1000 and the dehydrogenation metal is present in an amount of from 0.1 to 5.0 wt. %.

The feed preferably comprises a $C_6$/$C_7$ paraffinic naphtha containing paraffins and naphthenes, and wherein olefins may be present in the feed in an amount up to about 15 wt. %.

The first and second conversion zones preferably are separate conversion reactors selected from among fixed bed, fluidized or fluid transport type beds or a moving catalyst bed reactor. It is also preferred that the first and second reactors containing the first and second catalysts, respectively, are the same type of reactor. Alternatively, in a preferred embodiment the first and second conversion zones are within one reactor selected from among a fixed bed, fluidized or fluid transport type bed or a moving catalyst bed reactor.

It is also preferred that the temperature in the first and second conversion zones is from about 650° to about 1300° F., the pressure in the conversion zones is below about 400 psig, and the WHSV of the feed is from about 0.1 to about 15. Preferably, substantially no hydrogen is added to the feed.

The zeolite catalysts in the first and second conversion zones have silica to alumina ratios of at least 12, Constraint Indices of from 1 to 12 and crystal framework densities of not substantially below about 1.6 g/cc.

It is preferred to employ a matrix binder with either or both zeolite catalysts in the first and second conversion zones.

In one embodiment, it is also preferred to modify the noble metal component of the first conversion zone catalyst to its sulfide form by presulfiding the catalyst or adding at least one of $H_2S$, $SO_2$ or an organic sulfur compound to the feed in an amount effective to suppress hydrogenolysis and increase aromatic selectivity.

DETAILED DESCRIPTION OF THE INVENTION

It is contemplated that any nonaromatic $C_2$–$C_{12}$ paraffinic hydrocarbon may be used as feed to the conversion reactor in the process of this invention. A preferred feed comprises $C_6/C_7$ paraffinic naphtha containing paraffins and naphthenes, which may also contain relatively small amounts of aromatics. The aromatics are substantially inert with respect to the zeolite catalysts used herein. The following table demonstrates feedstock properties of a preferred $C_6/C_7$ light paraffinic naphtha feed:

| $C_6/C_7$ Light Paraffinic Naphtha Feedstock Properties | |
|---|---|
| Boiling Range | 180–250° F. |
| Density at 60° F. | 0.6914 |
| Hydrogen, wt. % | 15.55 |
| Sulfur, ppmw | 0.02 |
| Nitrogen, ppmw | <0.02 |
| Paraffins, wt. % | 81.3 |
| Naphthenes, wt. % | 13.3 |
| Aromatics, wt. % | 5.4 |
| $C_5$, wt. % | 2.7 |
| $C_6$, wt. % | 49.8 |
| $C_7$, wt. % | 47.2 |
| $C_8$, wt. % | 0.3 |

The maximum olefin concentration in the feed suitable for use in the present invention is 15 wt. %, and preferably less than 10 wt. %.

The conversion zones utilized in the process of the present invention are preferably fixed bed reactors, but may also be fluidized or fluid transport type catalyst bed or moving catalyst bed arrangements, including suitable combinations, if desired. Also, a reactor design comprising two catalyst beds within one reactor may be employed. In this case, the reactor may be any of a fixed, fluid or moving catalyst bed. However, although the present invention is sometimes described hereinafter as employing two separate reactors for convenience, it will be understood that the alternate reactor design comprising a first catalyst bed of a noble metal/low acidity medium pore size zeolite and second catalyst bed of an acidic medium pore size zeolite within one reactor is also within the scope of the present invention.

The above-described types of conversion reactors are generally known in the art. A heat exchange type tubular reactor configuration may also be employed. Appropriate heat exchange apparatus may be provided both within and outside the catalyst bed, as desired or as required by the particular reactor system. Since this particular hydrocarbon conversion reaction may be endothermic, exothermic or heat-balanced depending upon feed composition, provisions should be made for heat transfer within the system. This can be accomplished by indirect heat exchange with a suitable fluid. Heating, if needed, can be accomplished by direct firing as in a furnace. It can also be accomplished by direct heat exchange by means of the heated, regenerated catalyst and/or preheating of the feed, and/or heating or cooling a recycled stream. Aromatization reactions of saturated feeds are known to be highly endothermic and would therefore require significant heat input in some form or other. On the other hand, where the content of the feed would cause the conversion thereof to aromatics to be an exothermic reaction, the high temperatures achieved during operation of the process could cause an undesirable product distribution to be obtained, as well as resulting in high catalyst aging rates. Therefore, in an exothermic conversion reaction, it would be critical to the conversion process to provide sufficient heat removing or dissipating facilities, particularly during initial contact of the feed with the noble metal/low acidity zeolite conversion catalyst, so that the maximum temperature encountered in any portion of the conversion reactor is below an upper predetermined limit.

In the most preferred embodiments of the present invention, the second reactor bed should be the same type as the first reactor bed. It is even more preferred that the first reactor is of a fixed-bed design, and the second reactor is also a fixed-bed reactor.

It is well known that a medium pore size zeolite catalyst, such as ZSM-5, by itself, will convert paraffins to aromatics. However, the aromatic selectivity from paraffins is typically not greater than about 60 wt. %, since the acid function of the zeolite also produces methane and ethane, as illustrated in Table 1 below. It can also be demonstrated that the aromatic selectivity (defined as (wt. % aromatics produced)/(100-wt. % $C_2=+$) where $C_2=+$ is ethylene and high paraffins and olefins in the product) from ZSM-5 can be increased from about 60 wt. % to greater than 70 wt. % by adding a metal capable of providing a dehydrogenation function to the catalyst such as Zn or Ga, as also shown in Table 1.

TABLE 1

| | ZSM-5 | Zn/ZSM-5 | Ga/ZSM-5 |
|---|---|---|---|
| Temperature, °C. | 538 | 538 | 538 |
| WHSV | 0.7 | 1.4 | 0.4 |
| $H_2$ calc. | 0.5 | 2.1 | 3.7 |
| $C_1 + C_2$ | 25.0 | 14.7 | 21.1 |
| $C_2= +$ | 35.8 | 38.1 | 37.3 |
| Benzene | 9.7 | 14.1 | 12.1 |
| Toluene | 17.0 | 18.8 | 12.7 |
| $C_8$ Aromatics | 9.0 | 8.6 | 9.8 |
| $C_9 +$ Aromatics | 3.3 | 3.6 | 5.4 |
| Conversion | 64.2 | 63.6 | 62.7 |
| Aromatic Selectivity | 61 | 73 | 66 |

Aromatic selectivity is defined as (Wt. % Aromatics formed)/(100- wt. % $C_2= +$)

However, in accordance with the process of the present invention wherein the feed is passed over two different catalysts in two conversion zones, the aromatic selectivity is even further desirably increased by separating the dehydrogenation function and the acid function of the catalyst. Paraffin dehydrogenation and dehydrocyclization occur in the first reactor, and the unconverted olefins from the first reactor will be converted to aromatics in the second reactor. This specific process using the two types of catalysts described in detail hereinafter has not previously been known, and the present improved aromatization process is capable of obtaining significantly improved aromatic selectivity and thus higher gasoline octane (R+O), (M+O) and/or (R+M)/2. Even more increased aromatic selectivity is obtained in accordance with a preferred embodiment of the present invention, i.e., modifying the noble metal/low acidity medium pore size zeolite catalyst in the first conversion zone to its sulfide form by presulfiding or adding at least one of $H_2S$, $SO_2$ or an organic sulfur compound to the feed in an amount effective to suppress hydrogenolysis and further increase aromatic selectivity.

The catalyst in the first bed (or the first catalyst in a single reactor design) contains a noble metal, preferably a platinum group metal such as platinum, palladium, iridium, osmium, rhodium or ruthenium, in/on a low acidity medium pore size zeolite. This platinum group metal can be incorporated by ion exchange or impregnation to comprise about 0.01 to about 10 wt. %, preferably 0.1 to 3.0 wt. % based on the total weight of the metal and zeolite. The low acidity zeolite can be synthesized to have a low aluminum content, i.e., an $SiO_2/Al_2O_3$ ratio of greater than about 1000:1, or may be exchanged with group IA or IIA cations to reduce acidity to an alpha value of less than 5 in the absence of metals. As is known in the art, and as used in this application, the acidity of a catalyst may be measured by its alpha value. When alpha value is examined, it is noted that the alpha value is an approximate indication of the catalytic cracking activity of the catalyst compared to a standard catalyst and it gives the relative rate constant (rate of normal hexane conversion per volume of catalyst per unit time). It is based on the activity a highly-active silica-alumina zeolite cracking catalyst taken as an alpha of 1 (Rate Constant=0.016 $sec^{-1}$). In the case of zeolite HZSM-5, only 174 ppm of tetrahedrally coordinated $Al_2O_3$ are required to provide an alpha value of 1. The Alpha Test is described in U.S. Pat. No. 3,354,078, in *The Journal of Catalysis*, 6, pp. 522–529 (August 1965), and in *The Journal of Catalysis*, 61, p. 395 (1980), each incorporated herein by reference as to that description.

The catalyst in the second bed is a medium pore size acidic zeolite, such as ZSM-5, ZSM-11, ZSM-22, ZSM-23, ZSM-35 or ZSM-48. This zeolite catalyst should have an alpha value greater than about 10, and preferably between 50 and 1000. The acidic medium pore zeolite preferably contains a dehydrogenation metal, such as Zn, Ga, Sn or Cr which can be incorporated by ion exchange or impregnation to comprise about 0.01 to about 10 wt. %, preferably 0.1 to 5.0 wt. % of the total weight of the metal and the zeolite.

Accordingly, it will be understood that the basic zeolite catalyst (having a platinum group metal in the first reactor and preferably having in the second reactor a dehydrogenation metal such as Zn, Ga, Cr or Sn, incorporated therein/thereon by ion exchange or impregnation) used in both reactor beds can be the same, except for the acidity (alpha value). As noted, the first bed reactor zeolite catalyst desirably has a low acidity, i.e., an alpha value less than about 5, preferably less than one (1). The lower limit for alpha value of the zeolite can be defined in functional terms, i.e., alpha value can be as low as that which can be practically imparted to the zeolite and still achieve the objects of the present invention. It is difficult to define the exact lower limit of alpha value for low acidity zeolites useful in the present invention, because practical measurement becomes increasingly difficult at relatively low alpha value e.g., 0.001. The second bed zeolite catalyst has an alpha value of greater than about 10, preferably between 50 and 1000. The acidity (alpha value) of the two different zeolite catalysts can be modified to within these desired ranges, as would be easily recognized by one of ordinary skill in the art, by varying the silica to alumina ratio during synthesis of the zeolite and/or by exchanging the zeolite with group IA or IIA cations to reduce acidity, if necessary. However, the basic aluminosilicate zeolite to be modified in the above manner to satisfy the requirements of the first and second reactor beds can be chosen from members of the same class of zeolites, which class will be described in detail hereinafter, following the ensuing description of suitable process conditions.

In the process of the present invention, the conditions governing operation of the conversion process in the first and second conversion zones/reactors are generally selected from the same ranges as to temperatures, pressure and the WHSV of the feed. Preferably, the conditions are generally the same in the first and second conversion zones. Thus, suitable conditions are described below which are to be understood as applying to both conversion zones.

With respect to the conduct of the desired conversion reaction, the reaction temperature in both conversion zones will generally be from about 650° to about 1300° F. The pressure may be from about atmospheric up to several hundred pounds pressure, but below about 400 psig. The weight per hourly space velocity (WHSV) of the feed is usually within the range of about 0.1 to about 15 WHSV. If a moving catalyst bed is used, then the space velocities employed are those which give contact times equivalent to those which are obtained at space velocities of 0.1 to 15 WHSV for a fixed bed. These relationships are well known in the art.

The temperature at which the process is carried out is important and depends to a large extent upon the particular composition of feed material which is being charged to the catalysts. It has been discovered that there are certain minimum critical temperatures which must be employed in order to obtain the desired reaction and that these minimum temperatures have nothing to do with the concept of percent of conversion of the feed material but rather are concerned with the selectivity of the conversion of the feed material to aromatics. For the feed used in the process of the present invention, it has been determined that the minimum temperature which must be employed is 650° F. The upper limit of temperature is not narrowly critical and any practical upper maximum can be used which does not present problems with respect to heat input nor drive the reaction so far that the thermal cracking overrides the catalytic reforming conversion. In this connection, it has been found that a practical upper limit of temperature is about 1300° F.

The aromatization in accordance with the present invention preferably should be carried out in the absence of substantial amounts of added hydrogen. For reasons which are not completely understood, it appears that the addition of hydrogen in substantial amounts affects the ability of the medium pore size zeolite catalyst, such as a ZSM-5 catalyst, to catalyze the aromatization reaction so that an overall diminution of the catalytic activity of these materials is experienced. Therefore, it is preferred in carrying out the process that no added hydrogen be employed. Further, it should be noted that hydrogen is a by-product of the aromatization reaction and therefore there is always some hydrogen present during the course of the reaction. The hydrogen which is formed during the reaction does not seem to be adverse to the aromatization reaction. The aforementioned diminution in activity is apparent only when substantial amounts of hydrogen are added. It may very well be that the desire to minimize coke formation on the catalyst will dictate addition of small quantities of hydrogen. While this is not preferred, it is accepted where necessary.

Turning now to the basic medium pore size zeolites used in the present invention, the zeolite suitable for noble metal or dehydrogenation metal impregnation in the first and second reactors, respectively, may be selected from the class of zeolites described below, keeping in mind that the acidity of the catalyst in each conversion zone must be within the general confines outlined above. Suitable zeolites are members of a particular class of zeolites exhibiting some unusual properties, capable of inducing profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g., of the X and A type. Furthermore, carbonaceous deposits, when formed on the zeolite, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides a selective constrained access to, and egress from, the intra-crystalline free space by virtue of having an effective pore size between the small pore Linde A and the large pore Linde X, i.e., the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline aluminosilicate, the oxygen atoms themselves being bonded to the silicon (or aluminum, etc.) atoms at the centers of the tetrahedra. Briefly, the preferred zeolites useful as catalysts in this invention possess, in combination: a "Constraint Index" (defined hereinafter) of from 1 to 12; a silica to alumina ratio of at least about 12; and a structure providing a selective constrained access to the crystalline free space.

The silica to alumina mole ratio referred to may be determined by conventional analysis. This ratio is meant to represent, as closely as possible, the silica to alumina ratio in the rigid anionic framework of the zeolite crystal and to exclude aluminum which is present in the binder or which is present in cationic or other form within the channels. Although zeolites with silica to alumina mole ratios of at least 12 are useful, it is preferred to use zeolites having higher ratios of at least about 30. In some instances, zeolites having substantially higher silica/alumina ratios, e.g., 1600 and above, may be used.

Such zeolites, after activation, acquire an intracrystalline sorption capacity for normal hexane which is greater than that for water, i.e., they exhibit "hydrophobic" properties. It is believed that this hydrophobic character is advantageous in the present invention.

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA (tetramethyl ammonium) offretite does show some constrained access. Other 12-ring structures may exist which may be operative for other reasons, and therefore, it is not the intention of the present invention to entirely judge the usefulness of the particular zeolite solely from theoretical structure considerations.

A convenient measure of the extent to which a zeolite provides controlled access to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually pores of large size, e.g. greater than 8 Angstroms. The method by which Constraint Index is determined is described fully in U.S. Pat. No. 4,016,218, incorporated herein by reference for details of the method.

Constraint Index (CI) values for some typical materials, including some which are not within the purview of this invention, are:

|  | CI (at test temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |

| | CI (at test temperature) |
|---|---|
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the zeolites shown in the table above (including some outside the scope of the present invention), but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to one of ordinary skill in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest for use in the present invention within the approximate range of 1 to 12.

The class of zeolites defined herein is exemplified by ZSM-5, ZSM-11, ZSM-12, ZSM-22, ZSM-23, ZSM-35, ZSM-38, ZSM-48, Zeolite Beta and other similar materials.

ZSM-5 is more particularly described in U.S. Pat. No. 3,702,886 and U.S. Re. 29,948, the entire contents of which are incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-22 is more particularly described in U.S. Pat. Nos. 4,481,177, 4,556,477 and European Pat. No. 102,716, the entire contents of each being expressly incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

Zeolite Beta is taught in U.S. Pat. No. 3,308,069 and is taught as a catalyst component for isomerization dewaxing in U.S. Pat. 4,419,220 and 4,501,926. These disclosures are also incorporated herein by reference.

ZSM-48 is more particularly described in U.S. Pat. No. 4,397,827 the entire contents of which are incorporated herein by reference. The following description illustrates characteristics of zeolites useful in the present invention, using ZSM-48 as an example. This zeolite can be identified, in terms of moles of anhydrous oxides per 100 moles of silica, as follows:

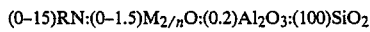

$(0-15)RN:(0-1.5)M_{2/n}O:(0.2)Al_2O_3:(100)SiO_2$ wherein:
M is at least one cation having a valence n; and
RN is a $C_1$–$C_{20}$ organic compound having at least one amine > functional group of $pK_a < 7$.

It is recognized that, particularly when the zeolite ZSM-48 composition contains tetrahedral framework aluminum, a fraction of the amine functional groups may be protonated. The doubly protonated form, in conventional notation, would be $(RNH)_2O$ and is equivalent in stoichiometry to $2 RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100 I/I_o$, where $I_o$ is the intensity of the strongest line or peak, and d (obs.), the interplaner spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | BROAD | PREFERRED |
|---|---|---|
| $Al_2O_3/SiO_2 =$ | 0 to 0.02 | 0 to 0.01 |
| $Na/SiO_2 =$ | 0 to 2 | 0.1 to 1.0 |
| $RN/SiO_2 =$ | 0.01 to 2.0 | 0.05 to 1.0 |
| $OH^-/SiO_2 =$ | 0 to 0.25 | 0 to 0.1 |
| $H_2O/SiO_2 =$ | 10 to 100 | 20 to 70 |
| $H+$ (added) $SiO_2 =$ | 0 to 0.2 | 0 to 0.05 | wherein RN is a $C_1$-$C_{20}$ organic compound having at least one amine functional group of $pK_a \geq 7$. The mixture is maintained at 80°-250° C. until crystals of the material are formed. H+ (added) is moles acid added in excess of the moles of hydroxide added. In calculating H+ (added) and OH values, the term acid (H+) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter the crystals are separated from the liquid and recovered. The zeolite composition can be prepared utilizing materials which supply the appropriate oxide. Such materials include sodium silicate, silica hydrosol, silica gel, silicic acid, RN, sodium hydroxide, sodium chloride, aluminum sulfate, sodium aluminate, aluminum oxide, or aluminum itself. RN is a $C_1$-$C_{20}$ organic compound containing at least one amine functional group of $pk_a \geq 7$, as defined above, and includes such compounds as $C_3$-$C_{18}$ primary, secondary, and tertiary amines, cyclic amines (such as piperidine, pyrrolidine and piperazine), and polyamines such as $NH_2$—$C_nH_{2n}$—$NH_2$ wherein n is 4–12.

Turning from the above detailed description of ZSM-48 to the general class of zeolites useful in the present invention, the original cations which may be in/on the zeolite crystal framework can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the zeolite class useful in the present invention with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation by reference of the above-identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The zeolites described above for use in the present invention, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type of zeolite. However, the presence of these cations does appear to favor the formation of this type of zeolite which is used in the present invention. More generally, it is desirable to activate this type of zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite brewsterite, stilbite, dachiardite, epistilbite, heulandite and clinoptilolite. The preferred crystalline aluminosilicates are ZSM-5, ZSM-11, ZSM-12, ZSM-22, ZSM-23, ZSM-35 and ZSM-48, with ZSM-5 particularly preferred. The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Group I through VIII of the periodic table. However, in the case of Group IA metals, the cation content should in no case be so large as to substantially eliminate the activity of the zeolite for the catalysts being employed in the second catalyst bed or second reactor. For example, a completely sodium exchanged H-ZSM-5 appears to be largely inactive for shape selective conversions such as those occurring in the second bed/reactor.

In a preferred aspect of this invention, the zeolites useful as catalysts herein are selected from those having a crystal framework density, in the dry hydrogen form, of not substantially below about 1.6 grams per cubic centimeter. It has been found that zeolites which satisfy all three of the discussed criteria (i.e., a Constraint Index of 1 to 12, a silica to alumina ratio of at least about 12, and a crystal framework density of not substantially below about 1.6 g/cc) are most desired for use in the present invention. When hydrocarbon products or by-products are catalytically formed, for example, such zeolites tend to maximize the production of gasoline boiling range hydrocarbon products. Therefore, the preferred catalysts of this invention are those comprising zeolites having a Constraint Index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article "Zeolite Structure" by W. M. Meier. This paper, the entire contents of which are incorporated herein by reference, is included in "Proceedings of the Conference on Molecular Sieves," (London, April, 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, seems to be important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

It is to be understood that the practice of the present invention is also applicable to isomorphs of the above-described crystalline aluminosilicate catalysts. For example, the aluminum may be replaced by elements such as gallium, and silicon by elements suh as germanium.

A matrix binder can be employed with both zeolite conversion catalysts. The matrix material should be resistant to the temperature and other conditions employed in the process of the present invention. The matrix binder imparts greater resistance to the catalysts for the severe temperature, pressure and reactant feed stream velocity conditions encountered in the process of the present invention. The catalyst can be incorporated, combined, dispersed, or otherwise intimately admixed with the matrix binder in such proportions that the resulting composite will contain from 1% to 95% by weight and preferably from 10% to 70% by weight of the zeolite catalyst in the final catalyst composite. A most preferred ratio is 65% by weight zeolite catalyst to 35% by weight matrix binder.

The term "matrix" includes inorganic compositions with which the zeolites can be incorporated, combined, dispersed, or otherwise intimately admixed with the catalyst wherein the matrix itself may be catalytically active or inactive, porous or non-porous. It is to be understood that the porosity of the composition employed as a matrix can be either inherent in the particular material or it can be introduced by mechanical or chemical means. Representative of matrices which can be employed include metals and alloys thereof, sintered metals, and sintered glass, asbestos, silicon carbide, aggregates, pumice, firebrick, diatomaceous earths, alumina and inorganic oxides. Inorganic compositions, especially those comprising alumina and those of a siliceous nature, are preferred. Of these matrices, inorganic oxides such as clay, chemically-treated clays, silica, silica alumina, etc., as well as alumina, are particularly preferred because of their superior porosity, attrition resistance and stability. Techniques for incorporating a zeolite catalyst into a matrix are known in the art and set forth in U.S. Pat. No. 3,140,253.

The improved aromatization process of the present invention can be characterized generally as a process whereby the paraffinic $C_2$-$C_{12}$ feed passes through the above-described two conversion zones containing the novel catalyst combination. However, even more improved results as to increased aromatic selectivity can be attained by modifying the noble metal/low acidity medium pore size zeolite first bed catalyst to its sulfide form to suppress hydrogenolysis, which is an unwanted side reaction which occurs during the production of aromatics and which reduces aromatic selectivity. This modification can be achieved in two ways, i.e., by "pre-sulfiding" the catalyst or by adding a sulfur-containing compound to the hydrocarbon feed. In either case, the noble metal is converted to its sulfide form. Presulfiding, as used herein, can be performed by treating the noble metal/low acidity zeolite catalyst with, e.g., 0.05 to 10 vol. % $H_2S$ in $H_2$ at high temperatures, e.g., 350°-500° C., for a sufficient amount of time to convert the noble metal to the sulfide form. At 500° C. and 2 vol. % $H_2S$ in $H_2$, the presulfiding treatment should be carried out for about 2 hours to ensure complete reaction. This can be confirmed by testing the gaseous effluent with lead acetate paper.

The noble metal/low acidity medium pore size zeolite first reactor catalyst can also be converted to the sulfide form by adding $H_2S$, $SO_2$ or an organic sulfur compound, such as dibenzothiophene, to the feed. Other suitable organic sulfur compounds include carbon disulfide, thiophene, dimethylsulfide and dimethyldisulfide, etc. The sulfur compound should be added to the feed in an amount effective to convert the noble metal to its sulfide form i.e., from about 15 to about 500 ppm (parts per million based on the total weight of the feed after sulfur addition) S (by wt.), preferably from 50 to 250 ppm S.

When the noble metal is converted to the sulfide form in accordance with this preferred aspect of the present invention, hydrogenolysis of the feed material, which is a major undesirable side reaction and leads to low aromatic yields, is suppressed and the aromatic selectivity is concomitantly increased. Thus, the aromatic selectivity of the catalyst employed in the first conversion zone is significantly improved by presulfiding the catalyst or by adding a sulfur-containing compound to the feed, as illustrated in the Examples of the present invention hereafter.

The reaction mixture recovered from the second reactor bed will contain both aliphatic and aromatic gasoline boiling range hydrocarbons, lighter aliphatic hydrocarbons and water. Product recovery may be by a series of unit operations employing a relatively simple condensation and decantation to separate a gaseous phase, a liquid hydrocarbon phase and an aqueous phase from each other. More specifically, the gaseous, liquid hydrocarbon and water phases may be separated by a conventional product separator, and the resulting gaseous and liquid hydrocarbon streams are sent to conventional petroleum fractionators for separation and stabilization, and the waste water phase is usually sent to a waste water treatment plant.

The present invention will now be described in the following Examples with reference to specific embodiments thereof which are not to be construed, however, as limiting the scope of the present invention in any manner whatsoever. For example, Pt/low acidity ZSM-5 will be used as the noble metal impregnated zeolite first bed catalyst, and Ga/Ti-ZSM-5 as the acidic medium pore second bed catalyst, to illustrate the present invention but it will understood that other zeolite catalysts as defined above could be used interchangeably with Pt/ZSM-5 and/or Ga/Ti-ZSM-5 and achieve similar results.

EXAMPLE 1

ZSM-5 having a silica to alumina ratio of 26,000:1, and an alpha value of about 1, was heated in $N_2$ at 2° C./min. to 538° C. for 2 hours, then held in air at 538° C. for 2 hours. The thus-calcined zeolite was treated with $Pt(NH_3)_4(NO_3)_2$ in D.I. (deionized) water at pH=9 for 2 hours at room temperature. The resulting Pt/ZSM-5 was further air calcined by heating at 2° C./min. to 350° C. and held for 2 hours. The resulting catalyst contained 0.7 wt. % platinum.

ZSM-5 having an $SiO_2/Al_2O_3$ ratio of 70:1 and an alpha value of 140 was treated with $TiCl_4(g)$ in $N_2$ at 350°–450° C. for 4–6 hours, then air calcined at 538° C. for 2 hours. The resulting Ti-ZSM-5 had an alpha value of about 39, and was then impregnated with $Ga(NO_3)_3$ and air calcined at 538° C. to form Ga/Ti-ZSM-5.

The dehydrocyclization yield obtained by passing a feed through a first conversion zone containing the Pt/low acidity ZSM-5 and then through a second conversion zone containing the Ga/Ti-ZSM-5 was tested with a $C_6/C_7$ naphtha feed comprising 81.3 wt. % paraffins, 13.3 wt. % naphthenes and 5.4 wt. % aromatics. The hydrocarbon distribution of the feed was 2.7 wt. % $C_5$, 49.8 wt. % $C_6$, 47.2 wt. % $C_7$ and 0.3 wt. % $C_8$.

In performing this test, the catalysts first were reduced in hydrogen at 350° C. for 1 hour, and then placed in separate beds and exposed to feed. Reaction conditions in both conversion zones were 538° C., atmospheric pressure, 2.4 WHSV overall and no added $H_2$. Since the overall WHSV is calculated using the total amount of catalyst in both conversion zones, the WHSV of the feed over each catalyst individually will be higher than the overall WHSV. In these Examples, the WHSV in the first conversion zone was calculated as 4.5, and the WHSV in the second conversion zone as 5.5 based on a constant feed space velocity (g/hr) through each conversion zone, but slightly less catalyst weight (g) in the second conversion zone. The reaction products were analyzed by on-line gas chromatography (GC) analysis.

The product distribution obtained with this catalyst combination is shown in Table 2 below. The aromatic selectivity is 78% in Example 1. This selectivity is higher than that for HZSM-5, Zn/ZSM-5 and Ga/ZSM-5, as shown in Table 1 above. The dual catalyst combination used in accordance with the process of the present invention is also more active, operating at 2.4 WHSV overall, compared to 0.7 WHSV for ZSM-5 and 1.4 WHSV for Zn/ZSM-5 (see Table 1 above).

EXAMPLE 2

This Example employed the same catalysts as described in Example 1 above, but at higher conversion (78.7 wt. %). The results as to aromatic selectivity and product distributions are also shown in Table 2 below.

EXAMPLE 3

This Example is representative of the preferred aspect of the process of the present invention in which the noble metal component of the first conversion zone catalyst is modified to its sulfide form by presulfiding or adding at least one of $H_2S$, $SO_2$ or an organic sulfur compound to the feed. This Example employs the same catalysts as in Examples 1 and 2, but 74 ppm S as dibenzothiophene were added to the feed. The data in Table 2 below demonstrate the further increased aromatic selectivity, i.e., from 78% to 84%, when sulfur was added to the feed.

TABLE 2

| Aromatic Selectivity (%) and Product Distributions (wt %) For Examples 1, 2 and 3* | | | |
|---|---|---|---|
| | Example 1 | Example 2** | Example 3 |
| $H_2$ | 3.5 | — | 3.7 |
| $C_1 + C_2$ | 10.5 | 14.1 | 7.2 |
| $C_2 + =$ | 36.4 | 21.3 | 30.5 |
| Benzene | 26.0 | 33.1 | 30.9 |
| Toluene | 19.1 | 23.1 | 21.5 |
| $C_8$ Aromatics | 1.3 | 5.3 | 3.0 |
| $C_9 +$ Aromatics | 3.2 | 3.2 | 3.2 |
| Conversion (wt % $C_2= +$) | 63.6 | 78.7 | 69.5 |
| Aromatic Selectivity | 78 | 82 | 84 |

*Reaction Conditions in each example were 538° C. atmospheric pressure, no added $H_2$, 4.5 WHSV over Pt/ZSM-5 and 5.5 WHSV over Ga/Ti-ZSM-5.
**Example 2 is not adjusted for $H_2$ balance. That is, while $H_2$ is a by-product of the reaction, the instrument employed to calculate product distribution in Example 2 is not capable of determining the amount of $H_2$.

Having thus generally described the process of the present invention and discussed specific embodiments in support thereof, it is to be understood that no undue restrictions as to the scope of the present invention are to be imposed by reason thereof.

What is claimed is:

1. In a process for converting a $C_2$–$C_{12}$ paraffinic hydrocarbon feed to aromatics by contacting the feed with at least one zeolite catalyst in a least one conversion zone, the improvement which comprises, passing the feed through a first conversion zone wherein the feed contacts a noble metal/low acidity medium pore size zeolite catalyst having an alpha value of less than about 5, and then passing the resulting hydrocarbon mixture through a second conversion zone wherein the resulting hydrocarbon mixture contacts a medium pore size acidic zeolite catalyst having an alpha value of greater than about 10.

2. The process according to claim 1, wherein said feed comprises a $C_6/C_7$ paraffinic naphtha containing paraffins and naphthenes, and wherein olefins may be present in the feed in an amount up to about 15 wt. %.

3. The process according to claim 2, wherein said amount is less than 10 wt. %.

4. The process according to claim 1, wherein said first and second conversion zones are separate conversion reactors selected from among fixed bed, fluidized or fluid transport type beds or a moving catalyst bed reactor.

5. The process according to claim 4, wherein the first and second reactors are the same type of reactor.

6. The process according to claim 5, wherein said first and second reactors are fixed bed reactors.

7. The process according to claim 1, wherein said first and second conversion zones are within one reactor selected from among a fixed bed, fluidized or fluid transport type bed or a moving catalyst bed reactor.

8. The process according to claim 7, wherein said reactor is a fixed bed reactor.

9. The process according to claim 1, wherein said noble metal/low acidity medium pore size zeolite catalyst contains a platinum group metal as the noble metal component selected from the group consisting of platinum, palladium, iridium, osmium, rhodium and ruthenium, said platinum group metal being present in an amount of from about 0.01 to about 10 wt. % based on the total weight of the metal and zeolite, and said low acidity zeolite has an alpha value of less than 5.

10. The process according to claim 9, wherein said platinum group metal comprises from 0.1 to 3.0 wt. %, and the low acidity zeolite has an alpha value of less than one.

11. The process according to claim 1, wherein said medium pore size acidic zeolite catalyst in the second conversion zone contains a dehydrogenation metal selected from the group consisting of Zn, Ga, Sn or Cr in an amount of from about 0.01 to about 10 wt. % based on the total weight of the metal and zeolite, and said acidic zeolite has an alpha value greater than about 10.

12. The process according to claim 11, wherein said dehydrogenation metal is present in an amount of from 0.1 to 5.0 wt. %, and the alpha value of the acidic zeolite is between 50 and 1000.

13. The process according to claim 1, wherein the temperature in the first and second conversion zones is from about 650° to about 1300° F., the pressure in said zones is below about 400 psig, and the WHSV of the feed is from about 0.1 to about 15.

14. The process according to claim 1, wherein substantially no hydrogen is added to the feed.

15. The process according to claim 1, wherein the zeolite catalysts in the first and second conversion zones have silica to alumina ratios of at least 12, Constraint Indices of from 1 to 12 and crystal framework densities of not substantially below about 1.6 g/cc.

16. The process according to claim 15, wherein said zeolite catalysts are selected from the group consisting of ZSM-5, ZSM-11, ZSM-12, ZSM-22, ZSM-23, ZSM-35, ZSM-38, ZSM-48 and Zeolite Beta.

17. The process according to claim 15, wherein said zeolite catalysts are ZSM-5.

18. The process according to claim 1, wherein a matrix binder is employed with either or both zeolite catalysts in the first and second conversion zones.

19. The process according to claim 1, which further comprises modifying the noble metal component of the first conversion zone catalyst to its sulfide form by presulfiding the catalyst or adding at least one of $H_2S$, $SO_2$ or an organic sulfur compound to the feed in an amount effective to suppress hydrogenolysis and increase aromatic selectivity.

20. The process according to claim 19, wherein said presulfiding comprises treating the noble metal/low acidity zeolite catalyst with 0.05 to 10 vol. % $H_2S$ in $H_2$ at a temperature of from 350°–500° C. for a period of time sufficient to convert the noble metal to its sulfide form.

21. The process according to claim 19, wherein said at least one of $H_2S$, $SO_2$ or an organic sulfur compound is added to the feed in an amount of from about 15 to about 500 ppm S by wt. based on the total weight of the feed after sulfur addition.

22. The process according to claim 21, wherein said at least one of $H_2S$, $SO_2$ or an organic sulfur compound is added to the feed in an amount of from 50 to 250 ppm S by wt.

23. The process according to claim 19, wherein said organic sulfur compound is selected from the group consisting of dibenzothiophene, carbon disulfied, thiophene, dimethylsulfide and dimethyldisulfide.

24. The process according to claim 1, wherein said noble metal/low acidity medium pore size zeolite catalyst has an alpha value of less than 1.

25. The process according to claim 1, wherein said medium pore size acidic zeolite catalyst has an alpha value between 50 and 1000.

26. The process according to claim 24, wherein said medium pore size acidic zeolite catalyst has an alpha value between 50 and 1000.

* * * * *